United States Patent [19]

Neumann

[11] 4,217,356
[45] Aug. 12, 1980

[54] 2-IMIDAZOLINYLAMINO-2,1,3-BENZO-THIADIAZOLES

[75] Inventor: Peter Neumann, Berne, Switzerland

[73] Assignee: Sandoz Ltd., Basel, Switzerland

[21] Appl. No.: 919,059

[22] Filed: Jun. 26, 1978

Related U.S. Application Data

[63] Continuation of Ser. No. 708,798, Jul. 26, 1976, abandoned.

[30] Foreign Application Priority Data

Aug. 22, 1975 [CH] Switzerland ............... 10911/75

[51] Int. Cl.² ............... A61K 31/415; C07D 417/04; A61K 31/425; C07D 417/10
[52] U.S. Cl. ............... 424/270; 548/126
[58] Field of Search ............... 260/304 D; 424/270; 548/126

[56] References Cited

U.S. PATENT DOCUMENTS 3,843,668  10/1974  Neumann ............... 260/304 D
4,053,617  10/1977  Eichenberger ............... 424/270

FOREIGN PATENT DOCUMENTS 2636309  3/1977  Fed. Rep. of Germany ...... 260/304 D

Primary Examiner—Alton D. Rollins
Attorney, Agent, or Firm—Gerald D. Sharkin; Richard E. Vila; Joseph J. Borovian

[57] ABSTRACT

This invention provides new compounds of formula I,

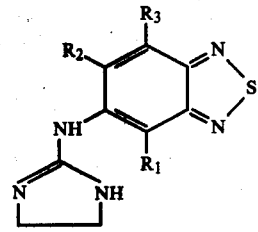

wherein
$R_1$, $R_2$ and $R_3$, independently, are hydrogen, halogen, nitro, cyano, hydroxy, alkyl, alkoxy or akylthio, wherein any alkyl moiety contains 1 to 4 carbon atoms, useful an anti-rigor agents, myotonolytics and muscle relaxants.

6 Claims, No Drawings

2-IMIDAZOLINYLAMINO-2,1,3-BENZO-THIADIAZOLES

This is a continuation, of application Ser. No. 708,798 filed July 26, 1976 now abandoned.

The present invention relates to 2,1,3-benzothiadiazole derivatives.

The present invention provides compounds of formula I,

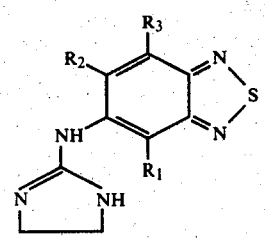

wherein $R_1$, and $R_2$ and $R_3$, independently, are hydrogen, halogen, nitro, cyano, hydroxy, alkyl, alkoxy or alkylthio, wherein any alkyl moiety contains 1 to 4 carbon atoms.

Halogen is fluorine, chlorine, bromine or iodine, preferably bromine or chlorine. Alkyl, alkoxy or alkylthio preferably has 1 or 2 carbon atoms. Preferably one or two radicals of $R_1$, $R_2$ and $R_3$ are hydrogen. $R_1$ is preferably halogen. $R_2$ is preferably hydrogen, halogen or methyl. $R_3$ is preferably hydrogen, chlorine or methyl.

The compounds of formula I may exist in the tautomeric form of formula Ia,

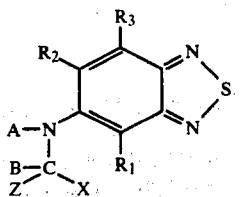

wherein $R_1$, $R_2$ and $R_3$ are as defined above.

For the sake of convenience compounds of formula I and Ia are defined herein as compounds of formula I. Similar considerations apply to the starting materials of formula II and III mentioned hereinafter.

The present invention provides a process for the production of a compound of formula I as defined above, which comprises:

reacting ethylene diamine with a compound of formula II,

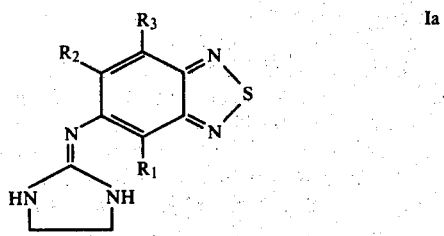

wherein $R_1$, $R_2$ and $R_3$ are as defined above, and
either A is hydrogen, and
B, Z and X, together with the carbon atom to which they are bound, is cyano, or
A and B together form a second bond between the nitrogen and carbon atom, and
X and Z, independently, form a leaving group, or a tautomer thereof.

The reaction may be conveniently effected in conventional manner for such reactions, e.g. as described in D.O.S. 2,322,880.

X and Z are either the same or different and may be $-S-R_4$, $-NH-R_4$, $-OR_4$ or $-NH-NO_2$, wherein $R_4$ is hydrogen or alkyl of 1 to 3 carbon atoms, or X and Z are identical and are, for example, chlorine. Preferably X is $-S-CH_3$ and Z is $NH_2$.

Preferably the compound of formula II is in the form of an acid addition salt, e.g. the hydrogen iodide and the ethylene diamine is in the form of the free base. Alternatively, preferably the compound of formula II is in free base form and the ethylene diamine is in the form of a mono-acid addition salt, e.g. the tosylate.

The reaction may conveniently be effected at a temperature between 0° and 200° C., preferably between 60° and 160° C. As solvents may be used alcohols with 1 to 8 carbon atoms, e.g. methanol, ethanol or n-pentanol, or dioxane, nitrobenzene or xylene.

The compounds of formula I may be isolated and purified in known manner.

Free base forms of compounds of formula I may be converted into acid addition salt form, e.g. the hydrochloride, hydrogen iodide, maleate, fumarate, methane sulphonate or tartrate, in conventional manner and vice versa.

It is supposed that the above process proceeds via an intermediate of a compound of formula III,

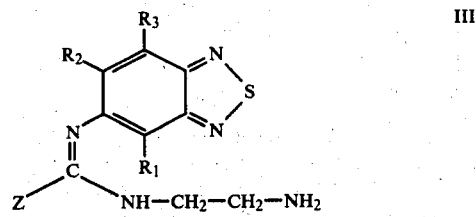

wherein $R_1$, $R_2$, $R_3$ and Z are as defined above, or a tautomer thereof, which cyclizes to form the compound of formula I. In another aspect the present invention provides a process for the production of a compound of formula I as defined above, which comprises cyclizing a compound of formula III, as defined above, or a tautomer thereof.

The reaction may be effected in known manner for such cyclizations. Considerations as regards preferred temperatures, solvents, and preferred values for Z are as mentioned above.

Preferably the compound of formula III is formed in situ from a compound of formula II, but may be produced from other compounds.

The starting materials of formula II may be produced in analogous manner to that described in D.O.S. 2,322,880.

In the following Examples all temperatures are in degrees Centigrade and are uncorrected.

EXAMPLE 1:
4-Chloro-5-(2-imidazolin-2-ylamino)-2,1,3-benzothiadiazole

A solution of 9.5 g of S-methyl-N-(4-chloro-2,1,3-benzothiadiazol-5-yl)-isothiouronium hydrogen iodide in 70 ml of methanol is treated with 1.7 ml ethylene diamine. The mixture is heated to boil for one hour. The solvent is subsequently concentrated by evaporation. The residue is treated with 10 ml of pentanol and heated to 150° C. for one hour. The cooled mixture is treated with 100 ml of ether. The resultant precipitate is filtered and washed with a little ether. The residue is dissolved in 70 ml of methanol. The solution is treated with active charcoal, filtered, made alkaline with 2 N aqueous sodium hydroxide, diluted with 100 ml of water and reduced to half the volume. After the mixture is cooled the resultant precipitate is filtered off, washed with water and boiled with 200 ml of methanol, yielding on cooling the title compound; M.Pt. 232°–235° C.

The starting material is obtained as follows: A solution of 6 g ammonium thiocyanate in 200 ml acetone is treated with 7 ml benzoyl chloride and stirred for 10 minutes. To this solution 6 g of 4-chloro-5-amino-2,1,3-benzothiadiazole in 200 ml of methanol is added. The mixture is boiled for 2 hours and cooled yielding N-benzoyl-N'-(4-chloro-2,1,3-benzothiadiazol-5-yl)thiourea (M.Pt. 220°–222° from methanol). The precipitate was filtered off and quickly heated to reflux with 100 ml of a 2 N aqueous solution of sodium hydroxide.

After 5 minutes the solution is cooled, filtered and made weakly acid with acetic acid. The formed precipitate is filtered off, washed with water, boiled with a little methanol, and washed with ether. The resulting N-(4-chloro-2,1,3-benzothiadiazol-5-yl)thiourea (M.Pt. 210°–213°) is boiled in 100 ml of methanol with 5 g methyl iodide for 1 hour. The mixture is then evaporated to dryness to yield crude S-methyl-N-(4-chloro-2,1,3-benzothiadiazol-5-yl)thiouronium iodide (M.Pt. 175°–179° C. from methanol), which is used directly in the next step.

EXAMPLE 2

In analogous manner to Example 1 the following compounds may be produced.
 (a) 5-(2-Imidazolin-2-yl-amino)-2,1,3-benzothiadiazole, M.Pt. 200°–201° C.
 (b) 4-Bromo-5-(2-imidazolin-2-yl-amino)-2,1,3-benzothiadiazole, M.Pt. 234°–236° C.

EXAMPLE 3

In analogous manner to that described in Example 1 there are prepared the following compounds of formula I, wherein:

|     | $R_1$ | $R_2$ | $R_3$ |
|-----|-------|-------|-------|
| (a) | $NO_2$ | Cl | Cl |
| (b) | Cl | CN | Cl |
| (c) | Cl | OH | Cl |
| (d) | Cl | $CH_3S$ | Cl |
| (e) | Cl | $CH_3O$ | Cl |
| (f) | Cl | Cl | $CH_3$ |

The compounds of formula I are useful because they exhibit pharmacological activity in animals. In particular, the compounds exhibit anti-rigor activity, e.g. for the treatment of rigor, as indicated by an inhibition of the rigor induced by Thalamonal in rats on i.v. administration of from about 0.001 to about 0.1 mg/kg in the test described in the above-mentioned D.O.S.

For the above-mentioned use the dosage will, of course, vary depending on the compound employed, mode of administration and therapy desired. However, in general, satisfactory results are obtained when administered at a daily dosage of from 0.001 mg to about 50 mg per kg animal body weight, conveniently given in divided doses 2 to 4 times a day or in sustained release form. For the larger mammal, the total daily dosage is in the range from about 10 to about 500 mg, and dosage forms suitable for oral administration comprise from about 2 mg to about 250 mg of the compounds admixed with a solid or liquid pharmaceutical carrier or diluent.

Additionally the compounds are useful as myotonolytics, e.g. for the treatment of spastic conditions, and as muscle relaxants, as indicated in standard tests; e.g. in rabbits on i.v. administration of from 0.001 to 0.1 mg/kg animal body weight a significant muscle relaxing effect is observed in accordance with the method of Teschendorf et al Arch. Exp. Pharmacol. 266, 467–468 (1970).

For the above-mentioned use the dosage will, of course, vary depending on the compound employed, mode of administration and therapy desired. However, in general, satisfactory results are obtained when administered at a daily dosage of from 0.0002 mg to about 1 mg per kg animal body weight, conveniently given in divided doses 2 to 4 times a day or in sustained release form. For the larger mammal, the total daily dosage is in the range from about 0.01 to about 10 mg, e.g. 0.1 and 6, preferably between 0.15 and 3 mg. Dosage forms suitable for oral administration conveniently comprise from about 0.0025 mg to about 5 mg of the compounds admixed with a solid or liquid pharmaceutical carrier or diluent.

The compounds of Examples 1, 2a and 2b exhibit especially interesting activity.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

I claim:
1. The compound of the formula

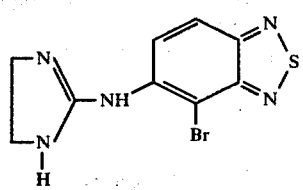

or a pharmaceutically acceptable acid addition salt thereof.

2. A pharmaceutical composition useful in treating spastic conditions, for relaxing muscles or in treating rigors comprising a pharmaceutically acceptable carrier or diluent and a therapeutically effective amount of the compound of claim 1 or a pharmaceutically acceptable acid addition salt thereof.

3. A method of treating spastic conditions which comprises administering to an animal in need of such treatment a therapeutically effective amount of the compound of claim 1, or a pharmaceutically acceptable acid addition salt thereof.

4. A method of relaxing muscles which comprises administering to an animal in need of such treatment a therapeutically effective amount of the compound of claim 1, or a pharmaceutically acceptable acid addition salt thereof.

5. A method of treating rigors which comprises administering to an animal in need of such treatment a therapeutically effective amount of the compound of claim 1, or a pharmaceutically acceptable acid addition salt thereof.

6. A method of relaxing muscles according to claim 4 which comprises administering to an animal in need of such treatment a therapeutically effective amount of 4-bromo-5-(2-imidazolin-2-yl-amino)-2,1,3-benzothiadiazole.

* * * * *

UNITED STATES PATENT AND TRADEMARK OFFICE
CERTIFICATE OF CORRECTION

PATENT NO. : 4,217,356

DATED : August 12, 1980

INVENTOR(S) : Peter Neumann

It is certified that error appears in the above—identified patent and that said Letters Patent is hereby corrected as shown below:

Title page, on the next-to-last line of the Abstract; delete "an" and insert in its place --as--.

Column 1, line 5; after "continuation", delete the comma.

Column 1, line 6; before "now", insert a comma.

Column 1, line 23; before "$R_2$", delete "and".

Signed and Sealed this

Twenty-fifth Day of August 1981

[SEAL]

Attest:

Attesting Officer

GERALD J. MOSSINGHOFF

Commissioner of Patents and Trademarks